(12) United States Patent
Takada et al.

(10) Patent No.: US 10,039,904 B2
(45) Date of Patent: Aug. 7, 2018

(54) GUIDE WIRE

(71) Applicant: ASAHI INTECC CO., LTD., Nagoya-shi, Aichi (JP)

(72) Inventors: Keigo Takada, Sakai (JP); Hirohiko Kobayashi, Mukou (JP)

(73) Assignee: ASAHI INTECC CO., LTD., Nagoya (JP)

(*) Notice: Subject to any disclaimer, the term of this patent is extended or adjusted under 35 U.S.C. 154(b) by 0 days.

(21) Appl. No.: 14/314,473

(22) Filed: Jun. 25, 2014

(65) Prior Publication Data
US 2015/0088036 A1 Mar. 26, 2015

(30) Foreign Application Priority Data
Sep. 25, 2013 (JP) ................. 2013-197685

(51) Int. Cl.
*A61M 25/09* (2006.01)

(52) U.S. Cl.
CPC ... *A61M 25/09* (2013.01); *A61M 2025/09083* (2013.01); *A61M 2025/09091* (2013.01); *A61M 2025/09133* (2013.01)

(58) Field of Classification Search
CPC .................... A61M 25/09; A61M 5025/09133
See application file for complete search history.

(56) References Cited

U.S. PATENT DOCUMENTS

| | | | |
|---|---|---|---|
| 5,840,046 A * | 11/1998 | Deem | A61M 25/09 600/585 |
| 6,340,441 B1 | 1/2002 | Meyer et al. | |
| 7,553,287 B2 | 6/2009 | Reynolds et al. | |
| 8,480,598 B2 | 7/2013 | Nelson, III et al. | |
| 2005/0096567 A1* | 5/2005 | Reynolds | A61M 25/09 600/585 |
| 2006/0047224 A1* | 3/2006 | Grandfield | A61M 25/09 600/585 |
| 2008/0004546 A1 | 1/2008 | Kato | |
| 2008/0183812 A1 | 7/2008 | Paul et al. | |

(Continued)

FOREIGN PATENT DOCUMENTS

CN 102205165 A 10/2011
EP 0 820 782 A2 1/1998

(Continued)

OTHER PUBLICATIONS

Dec. 17, 2014 Search Report issued in European Application No. 14173724.7.

(Continued)

*Primary Examiner* — Daniel Cerioni
*Assistant Examiner* — Yasmeen S Warsi
(74) *Attorney, Agent, or Firm* — Oliff PLC

(57) ABSTRACT

A guide wire includes a core shaft, a coil body which covers the core shaft, and a coating film which covers the coil body. Portions of the coating film are disposed between adjacent coils of coil body, and gaps are formed between the coils and the portions of the coating film disposed between the adjacent coils. Due to this configuration, the coating the film can be easily bent, and thus the coil body may easily bend. As a result, it is possible to ensure lubricity of guide wire within the blood vessel while also enabling the guide wire to follow the shape of the blood vessel in which it is inserted.

4 Claims, 4 Drawing Sheets

(56) References Cited

U.S. PATENT DOCUMENTS

| | | | |
|---|---|---|---|
| 2011/0245729 A1* | 10/2011 | Satozaki | A61L 31/10 600/585 |
| 2011/0245730 A1 | 10/2011 | Satozaki | |
| 2015/0088037 A1 | 3/2015 | Takada | |

FOREIGN PATENT DOCUMENTS

| | | |
|---|---|---|
| EP | 0982046 A1 | 3/2000 |
| EP | 1 243 283 A2 | 9/2002 |
| EP | 1 498 152 A1 | 1/2005 |
| EP | 1 875 941 A1 | 1/2008 |
| EP | 2371402 A2 | 10/2011 |
| JP | 2007509713 A | 4/2007 |
| JP | 2008011938 A | 1/2008 |
| JP | 2008-237621 A | 10/2008 |
| JP | 2011206494 A | 10/2011 |
| JP | 2016-027923 A | 2/2016 |
| JP | 2016-041349 A | 3/2016 |
| WO | WO 97/48330 A1 | 12/1997 |
| WO | 2004/007014 A1 | 1/2004 |

OTHER PUBLICATIONS

Aug. 29, 2014 Partial Search Report issued in European Patent Application No. 14173724.7.
Oct. 27, 2015 Office Action issued in Japanese Application No. 2013-197685.
Oct. 27, 2015 Office Action issued in Japanese Application No. 2013-197686.
Oct. 27, 2015 Office Action issued in Japanese Application No. 2013-197687.
Aug. 27, 2014 Extended Search Report issued in European Application No. 14173723.9.
Aug. 25, 2015 Office Action issued in U.S. Appl. No. 14/314,432.
U.S. Appl. No. 14/314,432, filed Jun. 25, 2014.
Nov. 6, 2015 Office Action issued in U.S. Appl. No. 14/314,657.
Aug. 1, 2014 Extended Search Report issued in European Application No. 14173720.5.
U.S. Appl. No. 14/314,657, filed Jun. 25, 2014.
Jan. 7, 2016 Office Action issued in European Patent Application No. 14 173 723.9.
Feb. 26, 2016 Office Action issued in Japanese Patent Application No. 2013-197687.
Feb. 22, 2016 Office Action issued in U.S. Appl. No. 14/314,432.
May 18, 2016 Office Action Issued in U.S. Appl. No. 14/314,657.
Nov. 15, 2016 Office Action issued in Japanese Patent Application No. 2015-229480.
Mar. 29, 2017 Office Action issued in Chinese Patent Application No. 201410279717.4.
Mar. 29, 2017 Office Action issued in Chinese Patent Application No. 201410279720.6.
Mar. 29, 2017 Office Action issued in Chinese Patent Application No. 201410280145.1.
Jul. 8, 2016 Office Action issued in Japanese Patent Application No. 2015-229480.
Jul. 8, 2016 Office Action issued in Japanese Patent Application No. 2015-229479.
Jul. 8, 2016 Written Directive issued in Japanese Patent Application No. 2015-229479.
Jul. 8, 2016 Written Directive issued in Japanese Patent Application No. 2015-229480.

* cited by examiner

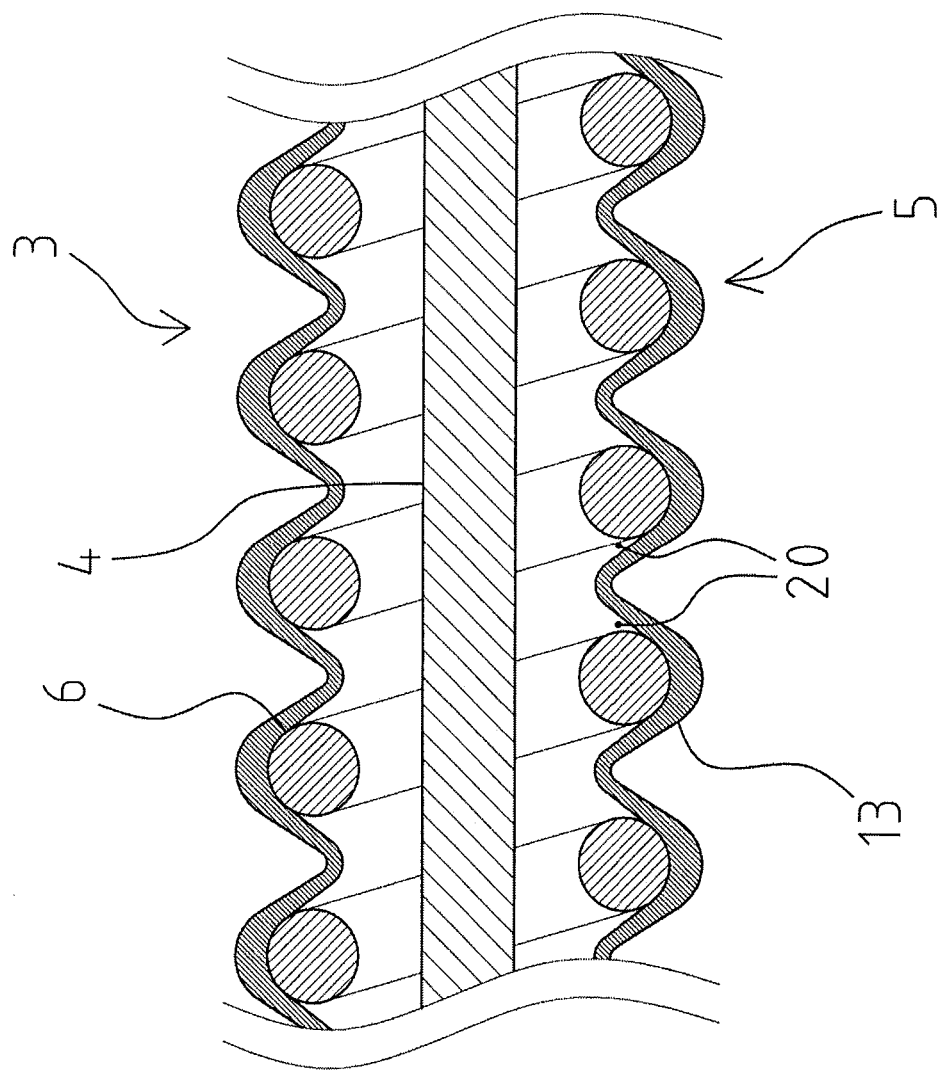

GUIDE WIRE

CROSS-REFERENCE TO RELATED APPLICATION

This application claims priority to Japanese Application No. 2013-197685 which was filed Sep. 25, 2013, the entire contents of which is hereby incorporated by reference.

BACKGROUND

The disclosed embodiments relate to a medical device. Specifically, the disclosed embodiments relate to a guide wire inserted into a lumen of a blood vessel or the like.

A guide wire used when inserting a catheter into a blood vessel is known. When inserting a catheter, first the guide wire is inserted into the blood vessel, and then the catheter is allowed to proceed along the guide wire. In such manner, the guide wire functions as a guide which guides the catheter to a lesion area.

A so-called coil-type guide wire having the distal end portion of its core shaft covered with a coil body is commonly used as such a guide wire. In addition, for the purpose of ensuring lubricity within the blood vessel, a guide wire having the surface of its coil body covered with a coating film made of a material such as resin has been proposed in U.S. Pat. No. 5,840,046.

SUMMARY

However, with the abovementioned conventional guide wire, when the surface of the coil body is covered with a coating film, it may become difficult to bend the coil body (and consequently the guide wire).

The disclosed embodiments have been devised in light of the abovementioned problem exhibited by conventional technology and an object of the present invention is to provide a guide wire that is easily bendable while the surface of its coil body is covered with a coating film.

In order to solve the abovementioned problem, a guide wire uses the following configuration. Namely, a guide wire comprises a core shaft, a coil body which covers the core shaft, and a coating film which covers the coil body, wherein portions of the coating film are arranged to come between adjacent coils of the coil body, and gaps are formed between the coils and the portions of the coating film that come between the coils.

In such a guide wire, when portions of the coating film are arranged to come between the coils of the coil body and gaps are formed between the coils and the portions of the coating film that come between the coils, it is possible for the coating film to easily bend when the coil body is bent. As a result, in the guide wire having the surface of its coil body covered with a coating film, the coil body (and consequently the guide wire) becomes easily bendable.

In addition, in the abovementioned guide wire, the portions of the coating film may be arranged such that they extend deeper than a center of a wire that forms the coils of the coil body.

In such a guidewire, when portions of the coating film are arranged to extend deeper than the center of the wire that form the coils of the coil body, the coating film is prevented from becoming fully stretched even when the coil body is bent (flexed) sharply. As a result, in addition to being easily bendable, it is possible to prevent the coating film from rupturing due to being fully stretched even when the guide wire is inserted into a bent region of a blood vessel.

In addition, because portions of the coating film extend deeper than the center of the wire forming the coils of the coil body, the adhesion of the coating film and the coil body may be improved, as will be described in more detail below.

In addition, in the abovementioned guide wire, the film thickness of the coating film in the portions that come between the coils of the coil body may be less than the coating film thickness in the portions that exist on the surface of the coil body.

In such a guide wire, because the film thickness of the coating film in the portions that come between the coils of the coil body is less than the film thickness of the portions that exist on the surface of the coil body, it becomes easier for the coating film to bend when the guide wire is bent. As a result, because the coil body (and consequently the guide wire) can be made to be more easily bendable, it is possible for the guide wire to excellently follow an intricately tortuous blood vessel.

Furthermore, the portions that exist on the surface of the coil body are easily worn due to contact with exterior items (such as the inner walls of blood vessels or lesions). Accordingly, due to the film thickness of such portions being greater, the guide wire may resist such wear.

BRIEF DESCRIPTION OF DRAWINGS

FIG. 4 is an enlarged view of the coil body and the coating film of a guide wire according to an exemplary embodiment.

DETAILED DESCRIPTION OF EMBODIMENTS

Various embodiments of a guide wire will be explained below.

Figure 1:
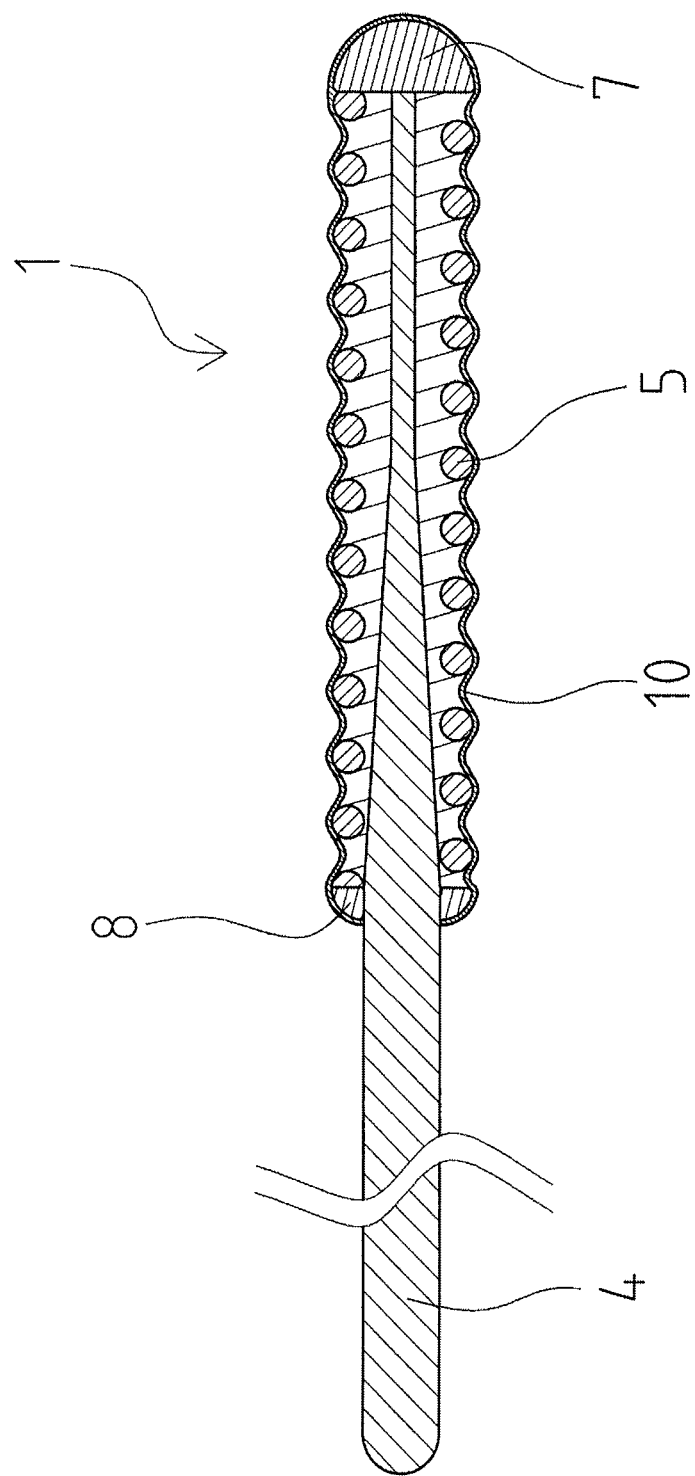
FIG. 1 is an explanatory diagram illustrating the configuration of a guide wire according to an exemplary embodiment.

FIG. 1 is an explanatory diagram illustrating the configuration of a guide wire (1). The guide wire (1) comprises a core shaft (4) and a coil body (5) which covers the core shaft (4). The distal end of the coil body (5) and the distal end of the core shaft (4) are connected via a joint (7) while the proximal end of the coil body (5) and an intermediate portion of the core shaft (4) are connected via a joint (8).

Furthermore, the surface of the coil body (5) is covered with a coating film (10). When the guide wire (1) is inserted into a blood vessel, the coating film (10) ensures lubricity by reducing the frictional resistance between the surface of the guide wire (1) and the inner walls of the blood vessel. Therefore, it is preferable that the coating portion (10) is formed of a material having a relatively low frictional resistance (such as a hydrophilic resin). For example, it is preferable that the coating portion (10) is formed with polyvinyl alcohol, polyvinyl pyrrrolidone, polyethylene glycol, polyacrylamide, polyacrylic acid, sodium polyacrylate, poly-(2-hydroxyethyl methacrylate), a maleic acid copolymer, an ethylene vinyl alcohol copolymer, a monomer of 2-methacryloyloxyethyl phosphorylcholine or a copolymer thereof, a (2-hydroxyethyl methacrylate)-styrene block copolymer, various synthetic polypeptides, collagen, hyaluronic acid, a cellulose-based polymer, or a mixture of any of these.

In addition, the coating portion (10) may also be formed using a material where an additive such as a non-hydrophilic monomer, a cross-linking agent, a non-volatile solvent, a volatile solvent, or a surfactant is added to any of the abovementioned materials.

Figure 2:
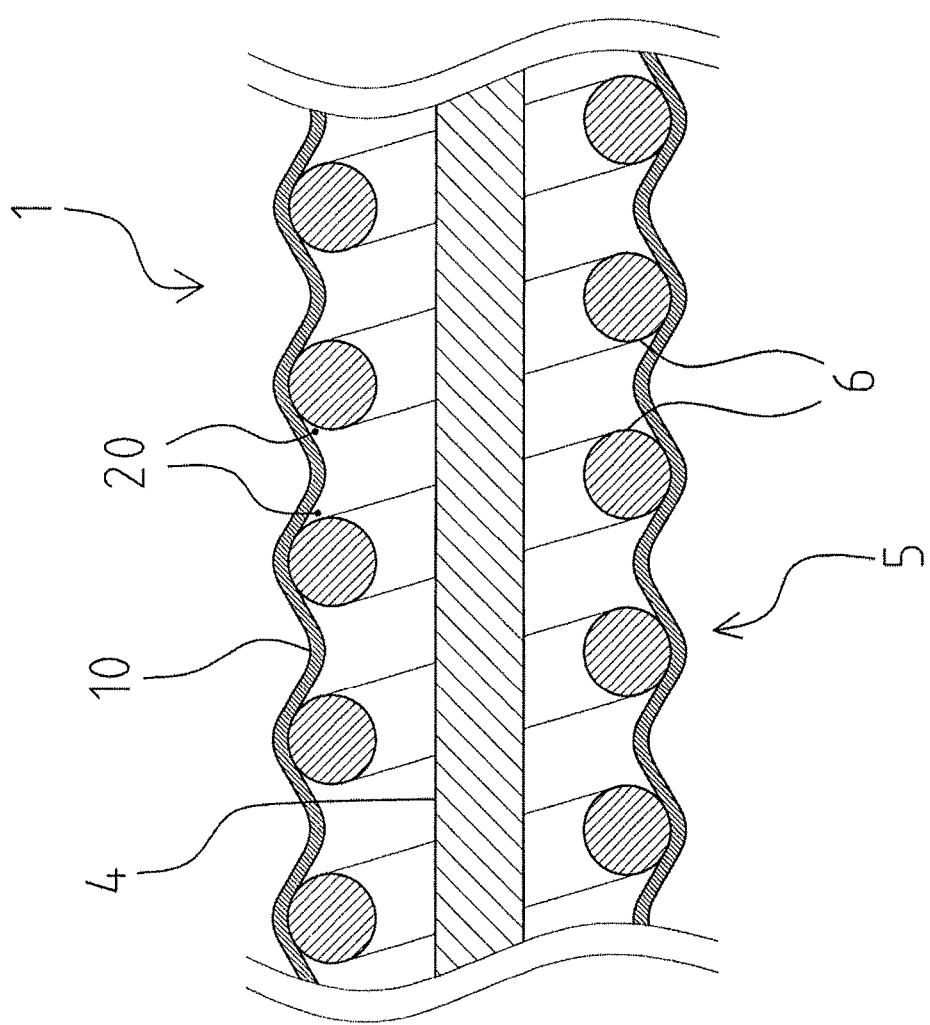
FIG. 2 is an enlarged view of the coil body and the coating film of the guide wire according to an exemplary embodiment.

FIG. 2 is an enlarged view of the coil body (5) and the coating film (10) of the guide wire (1). As illustrated in the drawing, the coil body (5) of the guide wire (1) of this embodiment is formed such that adjacent coils (6) (formed by one or more wires) are not in contact with each other. In other words, the coil body (5) is formed with a spread out pitch (open-coiled).

Furthermore, portions of the coating film (10) on the surface of the coil body (5) are arranged to come between adjacent coils (6) of the coil body (5). The coating film (10) is thus formed in a so-called bellows-shape.

In this configuration, gaps (20) are formed between the coils (6) of the coil body (5) and the portions where the coating film (10) comes into the spaces between the coils of the coil body (5). The reason for providing such gaps (20) in the guide wire (1) is explained below.

Namely, when there is no gap between the coils of the coil body and the portions where the coating film come between the coils of the coil body (for example, in a case where the gaps are filled due to the film thickness of the coating film being relatively thick), tension is created on the coating film when the coil body is bent. As a result, because the coil body (and consequently the guide wire) is difficult to bend, the ability of the guide wire to follow the shape of a blood vessel is lowered.

On the other hand, with the guide wire (1), because gaps (20) are formed between the coils (6) of the coil body (5) and the portions where the coating film (10) comes between the coils of coil body (5), it is easy for the coating film (10) to bend when the coil body (5) is bent. As a result, the coil body (5) may be easily bent.

As explained in the above, the coil body (5) of the guide wire (1) may be easily bent even with a configuration having the coating film (10) on the surface of coil body (5). For this reason, the guide wire's (1) lubricity within the blood vessel is ensured and the guide wire is also able to follow the shape of the blood vessel in which it is inserted.

Modifications of the guide wire (1) may be made without departing from the scope of the invention. In the following explanations, configurations that are identical to guide wire (1) are denoted by the same reference numerals and detailed explanations thereof are omitted.

Figure 3:
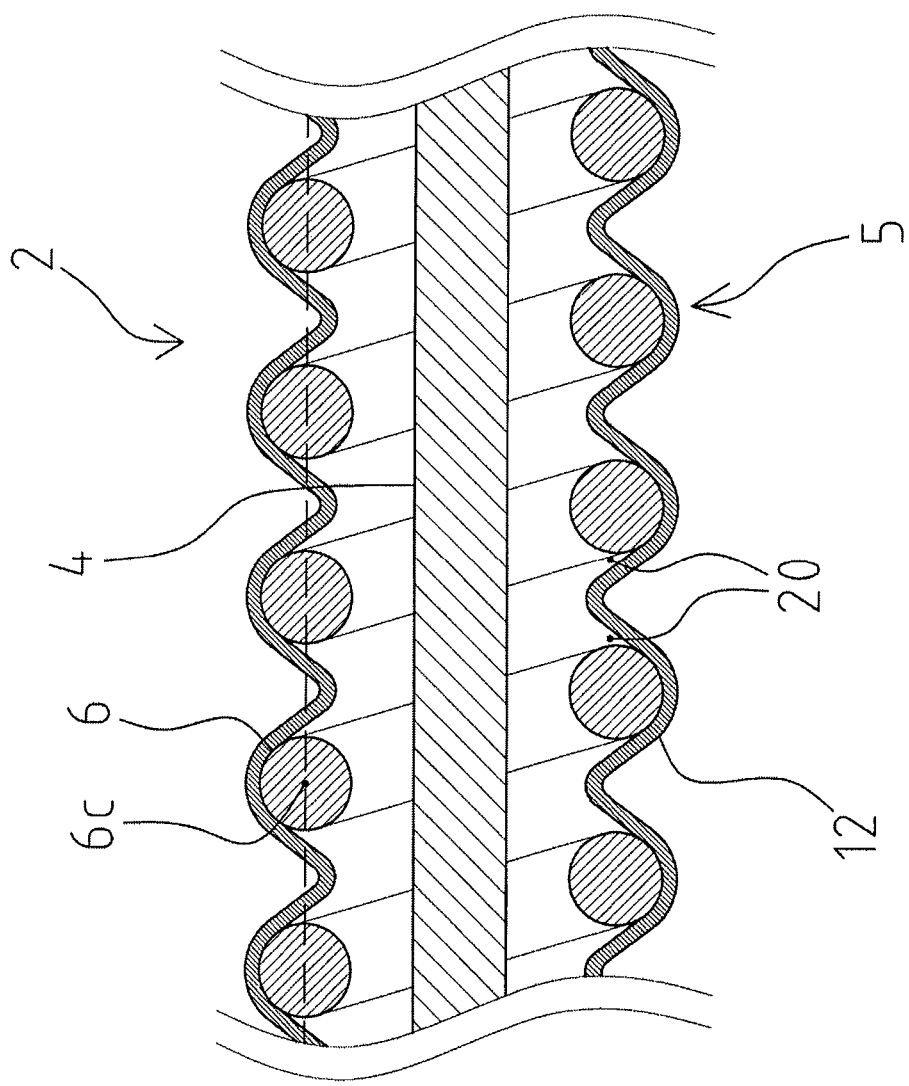
FIG. 3 is an enlarged view of the coil body and the coating film of a guide wire according to an exemplary embodiment.

FIG. 3 is an enlarged view of the coil body (5) and a coating film (12) of a guide wire (2). As illustrated in FIG. 3, portions of the coating film (12) which cover the coil body (5) are, in relation to the spaces between the coils (6) of coil body (5), arranged to come deeper than a center (6c) of the wire forming the coils (6). In other words, the depth of the extension of the portions of the coating film (12) from the surface of coil body (5) is greater than the radius of the wire forming the coils (6) of coil body (5).

Because the gaps (20) are formed between the coils (6) of the coil body (5) and the portions of the coating film (12) that come between the adjacent coils of coil body (5), the coil body (5) may be easily bent.

In addition, because the portions of the coating film (12) are, in relation to the spaces between the coils (6) of coil body (5), arranged to come deeper than the center (6c) of the wire forming the coils (6), the coating film (12) is prevented from being fully stretched even when the coil body (5) is greatly bent (flexed). Accordingly, it is possible to prevent the coating film (12) from rupturing due to being fully stretched even in a case where guide wire (2) is inserted into a bent region of a blood vessel.

Furthermore, as illustrated in FIG. 3, because the portions of the coating film (12) are, in relation to the gaps between the coils (6) of coil body (5), arranged to come deeper than the center (6c) of the wire forming the coils (6), it is possible to ensure a sufficient contact area between the coating film (12) and the coils (6) of coil body (5). As a result, it becomes possible to improve the adhesion of the coating film (12) and the coil body (5).

FIG. 4 is an enlarged view of the coil body (5) and a coating film (13) of a guide wire (3). In guide wire (3), the film thickness of the coating film (13) differs along the length of the guide wire (3). Namely, as illustrated in FIG. 4, the film thickness of coating film (13) in portions where the film comes between the coils of the coil body (5) is less than the film thickness of the coating film (13) in portions where the film exists on the surface of the coil body (5).

Similar to the abovementioned guide wire (1) and guide wire (2), because gaps (20) are formed between the coils (6) and the portions where the coating film (13) comes between the coils of the coil body (5), the coil body (5) may be easily bent.

Furthermore, it is possible for the guide wire (3) to excellently follow an intricately tortuous blood vessel. This is due to the following reason.

Namely, when the coil body (5) is bent, although the portions of the coating film (13) that exist on the surface of coil body (5) are barely subject to deformation, the portions of the coating film (13) that come between the coils of coil body (5) are subject to deformation. Accordingly, by reducing the film thickness of coating film (13) in such portions that are subject to deformation, the coating film (13) may more easily bend when the coil body (5) is bent. As a result, because it is easier to bend the coil body (5) (and consequently the guide wire (3)), the guide wire (3) may excellently follow an intricately tortuous blood vessel.

Meanwhile, the portions of the coating film (13) that exist on the surface of coil body (5) come into contact with exterior items (such as the inner walls of blood vessels or lesions) more frequently than the portions that come into the spaces between the coils (6) of coil body (5) and accordingly are more easily worn. With the guide wire (3), because the film thickness is greater in the portions that are more subject to wear (portions that exist on the surface of coil body (5), the resistance of the coating film (13) to such wear is improved.

Although various embodiments of the guide wire were explained above, the present invention is not limited to the abovementioned embodiments and it is possible to implement the present invention in various manners without departing from the scope thereof.

For example, with the abovementioned guide wires of the various embodiments, the coating film was explained as not being configured to come further inward than the inner peripheral surface of the coil body (refer to FIG. 2 through FIG. 4). However, this coating film may be configured to be arranged in a further inward position than the inner peripheral surface of the coil body (drawing omitted).

However, it is preferable that the coating film is arranged to not come too deep between the coils because this prevents the coating film from coming into contact with the core shaft when the guide wire is bent.

What is claimed is:
1. A guide wire comprising:
a core shaft;

a coil body that comprises a plurality of coils that covers the core shaft; and a coating film that covers the coil body, wherein:

adjacent coils of the plurality of coils are spaced apart, the coating film is bent towards the core shaft such that a first portion of the coating film and a second portion of the coating film are disposed between two adjacent coils, the first portion and the second portion being transverse to each other, the first portion of the coating film and a first coil of the two adjacent coils form a first gap and the second portion of the coating film and a second coil of the two adjacent coils form a second gap, the first gap and the second gap being disposed between the first coil and the second coil, the coating film is bent towards the core shaft such that a third gap is formed between the first portion and the second portion, the third gap being disposed between the first coil and the second coil such that the third gap is disposed on an opposite side of the coating film from the first gap and the second gap, and the coating film is bent towards the core shaft such that the coating film and the third gap extend deeper than a center of the adjacent coils.

2. A guide wire comprising:

a core shaft;

a coil body that comprises a plurality of coils that covers the core shaft; and a coating film that covers the coil body, wherein:

adjacent coils of the plurality of coils are spaced apart, the coating film is disposed between the adjacent coils such that gaps are formed between the coating film and the adjacent coils, and portions of the coating film that are disposed between the adjacent coils have a thickness that is less than a thickness of portions of the coating film that are disposed on the outer surface of the adjacent coils.

3. The guide wire according to claim 1, wherein the coating film is hydrophilic.

4. The guide wire according to claim 2, wherein the coating film is hydrophilic.

* * * * *